United States Patent [19]
Patel

[11] Patent Number: 6,143,302
[45] Date of Patent: Nov. 7, 2000

[54] HEADACHE AND COLIC RELIEF COMPOSITION WITH ASAFETIDA AND METHOD OF USE THEREOF

[76] Inventor: Sureshchandra K. Patel, 244 S. 17$^{th}$ St., St.Charles, Ill. 60174

[21] Appl. No.: 09/371,407

[22] Filed: Aug. 10, 1999

[51] Int. Cl.$^7$ ................................................. A61K 35/78
[52] U.S. Cl. ......................................................... 424/195.1
[58] Field of Search ........................................... 424/195.1

[56] References Cited

U.S. PATENT DOCUMENTS 119,179  9/1871  Randell .

OTHER PUBLICATIONS

Kahn, Pakistan Journal of Agriculture Research, vol. 6, No. 3, pp. 230–233, 1985.
Grant & Hackh's Chemical Dictionary—Fifth Edition p. 53 1987.
Webster's Third New International Dictionary p. 125 1993.
Webpage Text from Botanical.com—Asafetida 1999.
Webpage Text from www.herbaldare.com–Asafetida 1999.
Webpage Text from thriveonline.aol.com–Asafetida 1999.
Webpage Text from www.dubaicity.com–Asafetida 1999.
Webpage Text from www.patov.net–Herbs 1999.

*Primary Examiner*—Francisco Prats
*Assistant Examiner*—Susan D. Coe
*Attorney, Agent, or Firm*—Mark E. Wiemelt

[57] ABSTRACT

A chemical composition used as a topical treatment for relieving headache symptoms including *asafetida* and either water or a water based cream, if required. The chemical composition is created by mixing the ingredients to form a homogeneous paste. The chemical composition is then applied topically to the head, to the navel, or to both the head and to the navel to relieve headache symptoms.

6 Claims, No Drawings

HEADACHE AND COLIC RELIEF COMPOSITION WITH ASAFETIDA AND METHOD OF USE THEREOF

BACKGROUND OF THE INVENTION

1. Field of the Invention

This present invention relates to a chemical composition which relieves headache or colic symptoms. More specifically, the invention is directed to a chemical composition which is applied to the head or to the navel to relieve headache or colic symptoms.

2. Description of the Related Art

*Asafetida*, also called Food of the Gods and Devil's Dung, is a gum resin obtained from the plant *Feritla asafetida*. Prior uses of *asafetida* have been as a sedative and as a carminative to relieve colic and promote gas expulsion from the gastrointestinal tract. *Asafetida* has also been previously used as a drug to relieve convulsions and spasms, as a treatment for nerve disorders, as a stimulant to the brain and nervous system, and as a treatment for skin allergies.

There is a need in the art for a method for relief of headache or colic symptoms that provides relief quickly. There is also a need in the art for a method for relief of headache or colic symptoms which can be applied topically to skin and does not require that the method of relief be taken internally.

It is a primary object of the instant invention to provide a method for relieving headache symptoms.

A further object of the present invention is to provide a topical application method for relieving headache symptoms.

Another object of the instant invention is to provide a method for relieving headache symptoms which relieves headache symptoms expeditiously.

It is another primary object of the instant invention to provide a method for relieving colic symptoms.

Yet another object of the present invention is to provide a topical application method for relieving colic symptoms.

Still another object of the instant invention is to provide a method for relieving colic symptoms which relieves colic symptoms expeditiously.

These together with other objects of the invention, along with the various features of novelty which characterize the invention, are pointed out with particularity in the detailed description annexed to and forming a part of this disclosure. For a better understanding of the invention, its operating advantages and the specific objects attained by its uses, reference should be had to the descriptive matter in which is illustrated a preferred embodiment of the invention.

BRIEF SUMMARY OF THE INVENTION

According to the invention there is provided a chemical composition comprising *asafetida* which is to be applied topically to relieve headache or colic symptoms.

Further according to the invention there is provided a method for relieving headache or colic symptoms comprising applying the chemical composition topically to the navel and to the head.

Another embodiment of the present invention is diluting the chemical composition with water to form a homogeneous paste. This embodiment would achieve the same result as the prior embodiment.

A further embodiment of the present invention is diluting the chemical composition with water or a water based cream to form a homogeneous paste that is 60 to 90 percent *asafetida* by weight. This embodiment would also achieve the same result as the prior embodiment.

Another embodiment of the present invention is applying the chemical composition topically to the navel.

A further embodiment of the present invention is applying the chemical composition topically to the head.

There has thus been outlined, rather broadly, the more important features of the invention in order that the detailed description thereof that follows may be better understood, and in order that the present contribution to the art may be better appreciated. There are, of course, additional features of the invention that will be described hereinafter and that will form the subject matter of the invention. Those skilled in the art will appreciate that the conception, upon which this disclosure is based, may readily be utilized as a basis for other methods for carrying out the several purposes of the present invention. It is important, therefore, that the invention be regarded as including such equivalent constructions insofar as they do not depart from the spirit and scope of the present disclosure.

DETAILED DESCRIPTION OF THE PREFERRED EMBODIMENTS

While the invention may be susceptible to embodiments in different forms, there will be described in detail specific embodiments, with the understanding that the present disclosure is to be considered an exemplification of the principles of the invention, and is not intended to limit the invention to that as illustrated and described herein.

The chemical composition of the preferred embodiment of this invention includes *asafetida*. Nobody has discovered the extreme effectiveness of this chemical composition as a relief for headaches or colic symptoms until this invention. This is a new and novel use for this material.

The chemical composition is applied topically to the skin. More preferably the chemical composition is applied externally to the head or to the navel. Most preferably the chemical composition is applied to both the navel and the head. The chemical composition can be applied topically to the head or to the navel or to both with the hands and the fingers, with a towel, or with a sponge, but the application of the chemical composition to the skin is not limited to these types of applications. The chemical composition can then be rubbed into the skin on the head or the navel or both.

The chemical composition including *asafetida* can be combined with other materials in order to form a homogeneous paste. Most preferably the chemical composition including *asafetida* is mixed and diluted with water or a water based cream to form a homogeneous paste. The materials can be combined by sufficiently blending or mixing the materials. Most preferably, the *asafetida* is diluted with water or a water-based cream so that the resulting chemical composition is 60 to 90 percent by weight *asafetida*.

The following examples are intended to illustrate the invention without limiting the invention.

EXAMPLE 1

The *asafetida* is mixed with water or a water based solvent to create a chemical composition that is 90% pure *asafetida* by weight. The *asafetida* and the water or water based solvent are blended and must be mixed thoroughly to create a homogeneous paste. The resulting homogeneous paste can then be applied topically to the skin on the head, the navel, or both to provide relief from headache or colic symptoms. After application of the homogeneous mixture to the skin, the relief time from headache or colic symptoms is typically 5 to 10 minutes.

EXAMPLE 2

The procedure of Example 1 is repeated except that the chemical composition that results from the mixing of the *asafetida* and water or water based solvent is 80% pure *asafetida* by weight. After application of the paste to the skin, the relief time from headache or colic symptoms is typically 10 to 20 minutes.

EXAMPLE 3

The procedure of Example 1 is repeated except that the chemical composition that results from the mixing of the *asafetida* and water or water based solvent is 70% pure *asafetida* by weight. After application of the paste to the skin, the relief time from headache or colic symptoms is typically 20 to 30 minutes.

EXAMPLE 4

The procedure of Example 1 is repeated except that the chemical composition that results from the mixing of the *asafetida* and water or water based solvent is 60% pure *asafetida* by weight. After application of the paste to the skin, the relief time from headache or colic symptoms is typically 30 to 45 minutes.

While the invention has been described in connection with a preferred embodiment it will be understood that it is not intended that the invention be limited to that embodiment. On the contrary, it is intended to cover all alternatives, modifications and equivalents as may be included within the spirit and scope of the invention as disclosed.

As to the manner and usage and operation of the instant invention, same should be apparent from the above disclosure, and accordingly no further discussion relevant to the manner of usage and operation of the instant invention shall be provided.

With respect to the above description then, it is to be realized that the modifications of this chemical composition of this invention are deemed readily apparent and obvious to one skilled in the art, and all equivalent relationships are intended to be encompassed by the present invention.

Therefore, the foregoing is considered illustrative of only the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The foregoing discussion is illustrative of the invention. However, since many embodiments of the invention can be made without departing from the spirit and scope of the invention, the invention resides wholly in the claims hereinafter appended.

I claim:

1. A method of relieving colic symptoms comprising applying a chemical composition comprising *asafetida* topically to a user's skin.

2. The method of relieving colic symptoms as recited in claim 1, wherein said chemical composition is applied to the head.

3. The method of relieving colic symptoms as recited in claim 1, wherein said chemical composition is applied to the navel.

4. The method of relieving colic symptoms as recited in claim 1, wherein said chemical composition is applied to the navel and to the head.

5. A method of relieving headache symptoms comprising applying a chemical composition comprising *asafetida* to the navel.

6. A method of relieving headache symptoms comprising applying a chemical composition comprising *asafetida* to the navel and to the head.

\* \* \* \* \*